Figure 1:
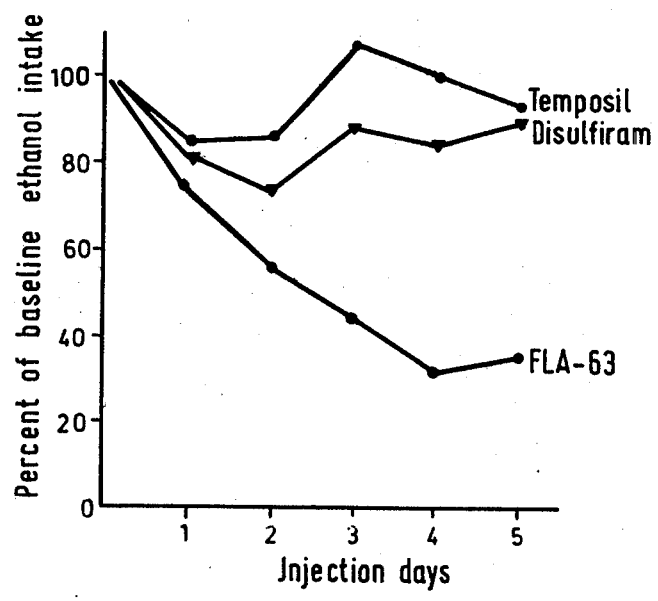

United States Patent [19]
Amit et al.

[11] 4,131,671
[45] Dec. 26, 1978

[54] METHOD OF TREATMENT

[75] Inventors: Zalman Amit, Montreal, Canada; Sven O. Ögren, Södertälje, Sweden

[73] Assignee: Astra Läkemedel Aktiebolag, Södertälje, Sweden

[21] Appl. No.: 812,690

[22] Filed: Jul. 5, 1977

[30] Foreign Application Priority Data

Jul. 5, 1976 [SE] Sweden .............................. 7607657

[51] Int. Cl.$^2$ ........................................... A61K 31/35
[52] U.S. Cl. .................................................. 424/244
[58] Field of Search ........................................ 424/244

[56] References Cited

U.S. PATENT DOCUMENTS 3,644,623  2/1972  Carlsson et al. ..................... 424/244

OTHER PUBLICATIONS

Collier, British Journal of Addiction, 1972, vol. 67, pp. 277–286.
Pozuelo, Cleveland Clinic Quarterly, vol. 43, No. 2, pp. 89–94 (Summer 1976 i.e. Jun. 21, 1976).

*Primary Examiner*—Donald B. Moyer
*Attorney, Agent, or Firm*—Brumbaugh, Graves, Donohue & Raymond

[57] ABSTRACT

A method for alleviating alcoholism comprising administering to a host in need of treatment an effective amount of the compound 4-methyl-1-homopiperazinedithiocarboxylic acid or a salt thereof, and a pharmaceutical preparation for alleviation of alcoholism comprising said compound or salt as an active ingredient.

6 Claims, 8 Drawing Figures

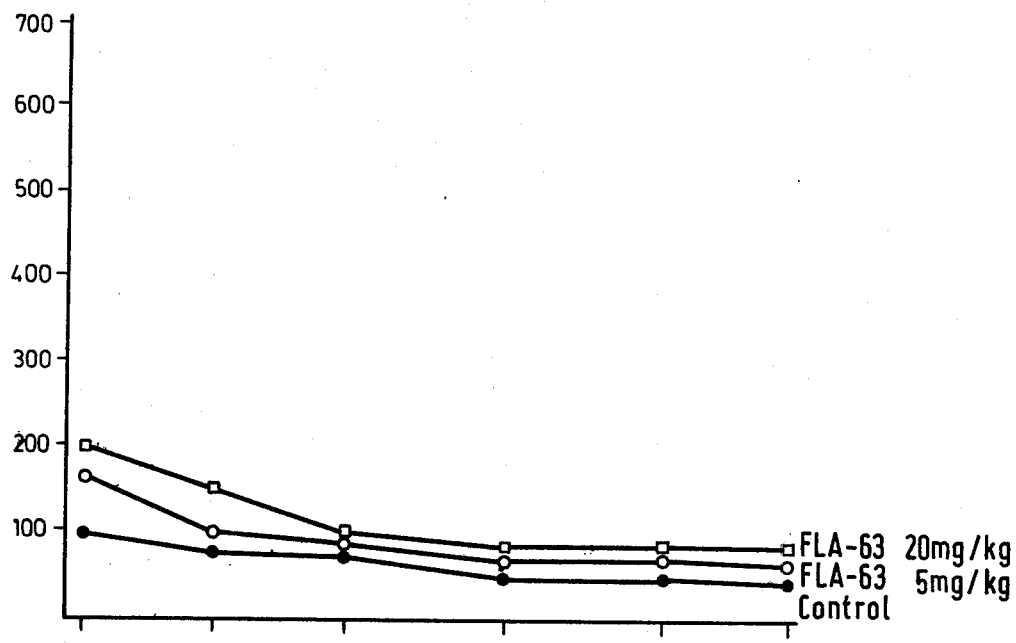
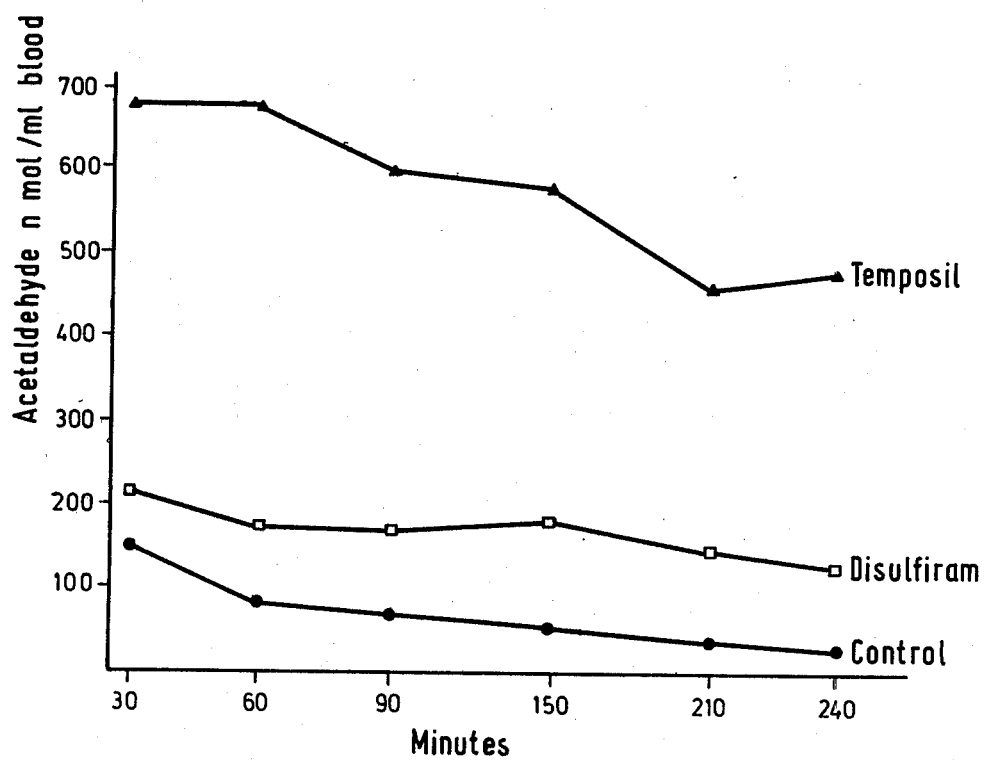
Fig. 2

Ethanol intake in terms of mean absolute ethanol consumption in rats subjected to extinction treatments (Tr) with FLA-57.

METHOD OF TREATMENT

The present invention is related to a new method of treatment of alcoholism or excessive consumption of ethanol in living beings including human beings, and to pharmaceutical preparations for such purpose.

An object of the invention is to provide a therapeutical agent effective in reducing the consumption of ethanol. A further object is to provide a therapeutical agent effective in alleviation of the disease known as alcoholism. Still further objects are to provide a therapeutical agent effective against the conditions mentioned without causing substantial aversion against ethanol and/or without affecting the habits of eating and non-alcoholic drinking.

BACKGROUND OF THE INVENTION

In the following ethanol is simply referred to as alcohol.

The drinking of alcohol is probably the oldest form of drug-oriented behaviour, dating back to the beginning of civilization. During the past few decades, a large variety of treatment procedures and treatment modalities were developed in the hope of controlling problem drinking. Such treatment procedures include the use of categories of drugs such as tranquilizers and anti-anxiety agents, anti-depressants, and mood-altering drugs. Another approach employed aversion-inducing drugs such as disulfiram (Bourne et al., Quarterly Journal of Studies on Alcohol, 27, 42–48, 1966) (disulfiram is also known under the trademark Antabuse ®) or citrated calcium carbimide (Mellor et al., British Journal of Addiction, 66, 123–128, 1971) (Temposil).

It is however known that such punishment is an ineffective means of modifying behaviour, and that pitting a competing behaviour against an existing drinking behaviour will also be an ineffective method of altering behaviour because of response competition. This leads to the conclusion that the primary task in developing an effective treatment procedure will be to extinguish rather than punish the drinking behaviour. In other words, the aim is to permanently alter behaviour, and not merely temporarily suppress an undesired response. There are, however, very few reports, if any, which have used an extinction technique for the treatment of alcohol. Attempts to extinguish alcohol drinking must, by definition, succeed in breaking the contiguity between performance of this act and its positive reinforcement. However, in the case of alcohol drinking, this has been a difficult if not impossible task. The primary reason for this difficulty is the fact that alcohol serves as its own reinforcer. In other words, the drinking of alcohol is reinforced by the drinking of alcohol.

In recent years, development in neurochemical techniques and in research on the physiological and biochemical basis of motivation and reinforcement produced data which may give us a channel through which it may become possible to separate the act of drinking alcohol from the reinforcement produced by this act. The term "reinforcement" refers to the process by which the frequency of a response is changed as a function of the contiguity between the response and its consequences. Certain behavioural events or environmental objects are called reinforcers because it has been observed that under the proper conditions they are highly efficient modifiers of behaviour. A widely held notion is that alcohol (and several other drugs) has positive reinforcing properties.

Since the discovery and anatomical definition of the catecholamine-containing central nervous system neurons numerous studies have been published which lend support to the notion that catecholamines are involved in the mechanisms of positive reinforcement.

It has been suggested that catecholamines may be involved in the reinforcing aspects of drug self-administration. Pozuelo et al., (Mayo Clinic Proceedings, 47, 621–628, 1972) demonstrated that treatment with alpha-methyl-paratyrosine (an inhibitor of catecholamine synthesis) blocked the self-administration of morphine in monkeys. Meade et al. (Paper presented at the meeting of the American Psychological Association, New Orleans, 1974) found that pretreatment with 6-hydroxydopamine (a neurotoxin which selectively destroys catecholamine-containing neurons) blocked the oral intake of morphine in rats. One must conclude that the disruption of drug self-administration seen following catecholamine depletion is due to an interference in the capacity of the animal to perceive the rewarding properties of the administered drugs.

Several recent studies suggest that the integrity of the catecholamine systems of the brain is important for the maintenance of alcohol self-administration as well. To illustrate, Amit et al. (Psychopharmacologia, 17, 367–377, 1970, and ibid. 21, 317–327, 1971) showed that electrical stimulation of the lateral hypothalamus (a catecholamine-containing region of the brain) elevated ethanol intake levels in rats. Furthermore, Kiianmaa et al. (Neuro-science Letters, 1, 41–47, 1975) and Myers et al. (Research Communications in Chemical Pathology and Pharmacology, 10, 363–378, 1975) reported that depletions of catecholamine produced by 6-hydroxydopamine modified ethanol consumption in rats.

Collier (British Journal of Addiction, 67, 277–286, 1972) suggested while examining the nature of the effect of disulfiram on alcohol drinking that it is possible that disulfiram exerts its effect via its capacity to interrupt the catecholamine metabolism. This notion is somewhat contrary to the commonly held view that the main effect of disulfiram stems from its inhibitory action an aldehyde dehydrogenase (which produces elevations in blood acetaldehyde levels and subsequently a toxic reaction).

Although some references thus suggest that alcohol-oriented behaviour may be modified by manipulation of the catecholamine systems, these suggestions have not hitherto led to a successful method of controlling alcohol drinking.

OUTLINE OF THE INVENTION

According to the present invention it has now been found possible to control alcohol drinking by administering to a host in need of treatment an effective amount of a compound active as an inhibitor of the enzyme dopamine-$\beta$-hydroxylase in the organism. Specifically the present invention provides a method for alleviating alcoholism comprising administering to a host in need of treatment an effective amount of the compound 4-methyl-1-homopiperazinedithiocarboxylic acid or a salt thereof, defined by the structural formula

wherein R is hydrogen, sodium, potassium, ammonium or another nontoxic cation. Said compounds are known from the specification and claims of U.S. Pat. No. 3,644,623, the contents of which are incorporated by reference herein. The compound in which R is hydrogen is hereinafter referred to as FLA-57.

The present invention thus provides a method of alleviating alcoholism, comprising administration to a host in need of such alleviation an effective amount of a compound defined above. In more general terms the invention provides a method of reducing alcohol comsumption in living beings. As will be disclosed below the present invention provides methods of treatment which do not cause substantial aversion against alcohol and which do not substantially affect the habits of eating and non-alcoholic drinking.

The dosis of administration of the compound employed according to the invention depends i.a. on route of administration and form of pharmaceutical preparation. In general the dosis may vary from 0.5 to 7 mg per kg bodyweight in human beings. A suitable dosis may be about 1-2 mg/kg or about 100-200 mg per day. The treatment according to the invention may suitably extend for a period of about 1 to 6 weeks, preferably 10 to 20 days.

METHODS OF PREPARATION OF THE COMPOUNDS UTILIZED

The compounds employed according to the invention may be prepared by reacting the compound

with carbon disulphide only or in the presence of a compound of the formula $R^oZ$, wherein $R^o$ denotes sodium or another non-toxic cation and Z denotes an anion such as e.g. $OH^-$, $CO_3^{2-}$ and the like for the formation of a compound of the general formula

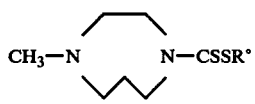

which thereupon, if compounds are desired where R denotes hydrogen. is reacted with an acid.

The starting material of the formula

may be manufactured in many different ways. The following reaction scheme could preferably be followed:

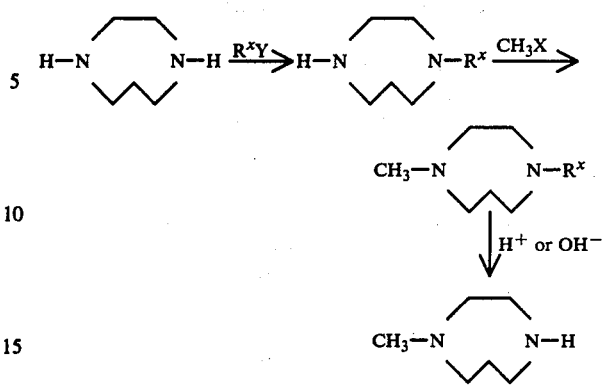

wherein $R^x$ denotes a protecting group such as for example an alkoxycarbonyl, benzyl, trityl, acyl, nitroso or sulphonyl group.

It is advisable to start with the hemisalt of homopiperazine, and the reaction then will be the following one:

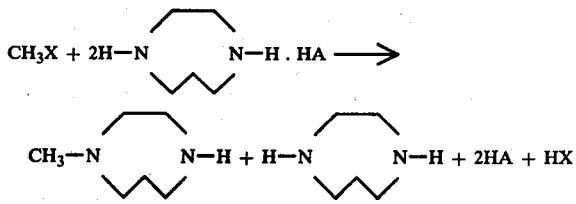

where HA denotes an inorganic or organic acid.

At the reaction between the amine

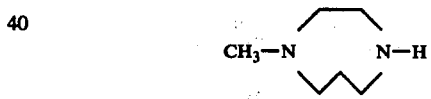

and carbon disulphide in an inert solvent such as e.g. ether, the free acid is obtained.

The free acid here above, which is present as an internal salt

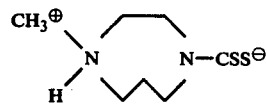

may then, if a compound is desired in which R denotes sodium or another non-toxic cation other than hydrogen, be reacted with for example the hydroxide of the desired cation in an equivalent quantity, and the corresponding salt will be formed.

For a direct formation of the compound

wherein R denotes sodium or another non-toxic cation the amine

is reacted with carbon disulphide in the presence of for example the hydroxide of the desired cation. The salt thus formed may then if the free acid is desired be reacted with an acid such as for example acetic acid, and the free acid will be precipitated as an internal salt.

Preparation of the compound FLA-57 and a salt thereof is illustrated by the following examples.

EXEMPLE 1

30.0 grams (0.263 moles) of 1-methylhomopiperazine dissolved in 150 millilitres of ether were added, drop by drop to 25 millilitres of carbon disulphide dissolved in 150 millilitres of ether. The precipitate obtained was sucked off and washed with ether. The residue, 39 grams of 4-methyl-1-homopiperazinedithiocarboxylic acid, had a melting point of 200°–202° C. (subl).

EXAMPLE 2

57.0 g (0.3 moles) of 4-methyl-1-homopiperazinedithiocarboxylic acid (FLA-57) was dissolved in 300 ml of water with 12.0 g (0.3 moles) of NaOH. The solution was evaporated. The residue was recrystallized from ethanol-isopropyl ether, 37.5 g of sodium 4-methyl-1-homopiperazinedithiocarboxylate monohydrate was obtained. Mp 123°–125° C. elemental analysis. C calculated 36.60%, found 36.5%, H calculated 6.56%, found 6.54%, N calculated 12.16%, found 12.1%, S calculated 27.84%, found 27.8%.

PHARMACEUTICAL PREPARATIONS

In clinical practise the compounds of the invention will normally be administered orally, rectally or by means of an injection in the form of pharmaceutical preparations comprising a therapeutically active quantity of at least one of the compounds incorporated in a pharmaceutically acceptable carrier and that may comprise a solid, a semi-solid or a liquid diluent or a capsule. These preparations normally contain between 0.1 and 95% by weight of the active compound, e.g. between 0.5 and 20% by weight for preparations intended for injections and between 2 and 50% by weight for preparations intended for oral administration.

To produce pharmaceutical preparations containing a compound of the present invention, in the form of dosage units for oral administration, such a compound may be mixed with a solid pulverulent carrier, e.g. lactose, saccharose, sorbitol, mannitol, starch such as potato starch, corn starch, amylopectin, laminaria powder or a citrus pulp powder, cellulose derivatives or gelatin, and may also include a lubricant such as magnesium or calcium stearate or a Carbowax or another polyethylene glycol wax and then compressed to form tablets. When coated tablets are required, the cores may be coated with a concentrated sugar solution which may contain e.g. gum arabic, gelatin, talcum and/or titanium dioxide. Alternatively, the tablets may be coated with a lacquer dissolved in a volatile organic solvent or a mixture of organic solvents. Dyestuffs may be added to these coatings e.g. for distinction between tablets containing different contents of the active compound. For the preparation of soft gelatine capsules (pearl-shaped closed capsules) consisting of gelatin and for example glycerol and similar closed capsules the active substance may be admixed with a vegetable oil. Hard gelatin capsules may contain granulates of the active substance in combination with solid pulverulent carriers such as lactose, saccharose, sorbitol, mannitol, starches (e.g. potato starch, corn starch or amylopectin), cellulose derivatives or gelatin. Dosage units for rectal administration may comprise suppositories comprising the active compound in admixture with a neutral fatty base, or gelatin capsules comprising the active compound in admixture with vegetable oil or paraffin oil.

Liquid preparations for oral administration may be in the form of syrups or suspensions, for example, solutions containing from about 2 to 20% by weight of the active compound, sugar and a mixture of ethanol, water and glycerol, propylene glycol and in addition flavouring agents, saccharine and/or carboxymethyl cellulose as a thickening agent.

For parenteral administration by means of injection the preparations according to the invention preferably comprise an aqueous solution of the active compound preferably in a concentration of 0.5–10% by weight and further a stabilizing agent and/or buffering agent. For convenient reasons it might be desirous to enclose the dosage units of the solution in ampoules.

PHARMACOLOGICAL TESTS

In the first phase of this project, we examined the relative efficacies of an aldehyde dehydrogenase inhibitor (citrated calcium carbimide; Temposil), a dopamine-beta-hydroxylase inhibitor (bis(4-methyl-homopiperazinyl-thiocarbonyl)-disulfide; FLA-63) and disulfiram to modify the voluntary consumption of ethanol in laboratory rats. Animals were maintained on an alternate day regimen of ethanol presentation, with tap water available at all times. Rats were first exposed to an ascending series of ethanol concentrations in a free choice with tap water, until they were consistently drinking 50% or more of their fluid intake as ethanol. The range of concentrations of final ethanol solutions was 6%–30%. Once a stable intake of ethanol had been established, animals received a total of 5 i.p. injections of either Temposil (25mg/kg), disulfiram (25mg/kg) or FLA-63 (20mg/kg) on the days when ethanol was available to them. As can be seen from FIG. 1, Temposil had virtually no effect on ethanol drinking. In the case of disulfiram, the maximal suppression of ethanol intake occurred following the third injection, when ethanol intake was reduced by about 20%. By the fourth injection, ethanolintake was gradually returning to baseline levels. By far the greatest suppression of ethanol intake was observed following injections of FLA-63. Ethanol intake fell steadily throughout the injection period, so that by the fourth injection day rats were drinking at less than 40% of preinjection levels.

On the basis of these findings, in particular that Temposil did not interfere with voluntary ethanol drinking while presumably raising blood acetaldehyde levels, it was decided to examine blood acetaldehyde levels following injections of Temposil, disulfiram and FLA-63. Rats received 1.5 g EtOH/kg body weight, administered as a 10% solution. Disulfiram (50 mg/kg) was administered twice, 20 hours and 1 hour prior to ethanol injections. FLA-63 (5 mg/kg and 20 mg/kg dissolved in 1N acetic acid and neutralized with 1N NAOH) was given immediately following ethanol injections. Temposil (25 mg/kg) was also given 20 hours and 1 hour before ethanol injections. Control subjects were injected with a 1N acetic acid/1N NAOH vehicle solution. Blood acetaldehyde levels were determined by gas-liquid chromatography from blood samples drawn at 30 minute intervals from the tip of the tail.

Blood acetaldehyde levels in the rats receiving 20 mg/kg of FLA-63 were significantly higher than vehicle controls ($p < .05$) only at the first 30 minute interval sampled (see FIG. 2). The 5 mg/kg dose of FLA-63 did not significantly alter blood acetaldehyde levels. Much more dramatic elevations in blood acetaldehyde levels were obtained from injections of disulfiram and Temposil. Disulfiram raised blood acetaldehyde levels up to 3 times the value of controls, while Temposil produced even greater elevations, up to seven times the value of controls. The difference between Temposil, disulfiram and control levels were highly significant at almost all time intervals.

The results of this study tend to support the notion that inhibition of dopamine-beta-hydroxylase and the resultant depletion of brain norepinephrine may play an important role in suppressing voluntary ethanol intake in rats and possibly also in humans. The data indicate that FLA-63 is a less potent elevator of blood acetaldehyde than the other two compounds employed, but at the same time has the largest effect on voluntary ethanol intake. The results thus suggest that FLA-63 suppresses ethanol intake by a mechanism different from that acetaldehyde-elevating mechanism, possibly through the known inhibition of dopamine-beta-hydroxylase.

At this point in time we began our investigations with FLA-57. Toxicity problems which arose with FLA-63 bring special attention to any study that employs pharmacological or neurochemical agents in a paradigm where the dependent variable is a consummatory response. This issue refers to non-specific effects of compounds which artifactually may affect the tendency of an animal to ingest alcohol, food of water. These non-specific effects include finickiness, general motor ataxia, and the possibility that neurochemical agents are capable of producing a learned taste aversion when paired with the drinking of alcohol. In regard to the latter point, a reduction in alcohol intake due to a conditioned taste aversion must be considered artifactual in the context of this study, since this drop in drinking cannot be attributed to interference with the positive reinforcing properties of alcohol. In this context, the first phase of the FLA-57 experimentation involved an examination of the effects of FLA-57 on eating, drinking and body weight maintenance, since we had observed considerable non-specific toxic effects with FLA-63.

In this phase of the study, we employed two dose levels of FLA-57, 25 mg/kg and 40 mg/kg. These doses were chosen on the basis of the relative efficacy and toxicity of FLA-57 and FLA-63. For a period of five days, baseline levels of food intake, water intake and body weight were recorded. At this time animals were divided into two groups and received a total of 5 i.p. injections of either dose, spaced over a 10 day period. As can be seen from FIGS. 3 & 4 5 injections of FLA-57 had absolutely no effect on food intake, water intake or body weight. It should be pointed out that the vehicle for FLA-57 was buffered to pH 8.00, as opposed to pH 7.00 used for FLA-63. As well, care was taken to inject the drug within 15 minutes of its preparation as an injectable solution.

After it had been established that FLA-57 would not interfere with general consummatory behaviours, studies were commenced to examine the effects of FLA-57 on ethanol intake. In this portion of the programme, the following paradigm was adhered to: The previous dose levels of FLA-57 were used, and a control group was added, which received vehicle injections consisting of a 1N NAOH/1N acetic acid solution buffered to pH 8.00-8.20. Individual test concentrations of ethanol were established as described previously. Ethanol was presented every second day in a free choice with tap water, and injections were administered on ethanol days, 4 hours prior to ethanol presentation. After establishing a baseline of ethanol intake, the three groups of animals received a dose of either FLA-57 or vehicle over a 10-day period. Then followed an 8 day no-injection period, during which time animals were maintained on an alternate day schedule of ethanol presentation in a free choice with tap water. Animals then received another 5 injections spaced over a 10-day period. (The time parameters were chosen because we observed that 5 such injections of FLA-63 produced marked signs of toxicity in rats. In fact, in the long term phases of these studies, animals received as many as 20 FLA-57 injections, without any observable signs of non-specific effects). Finally, another 10-day no-injection period followed.

Figure 3:
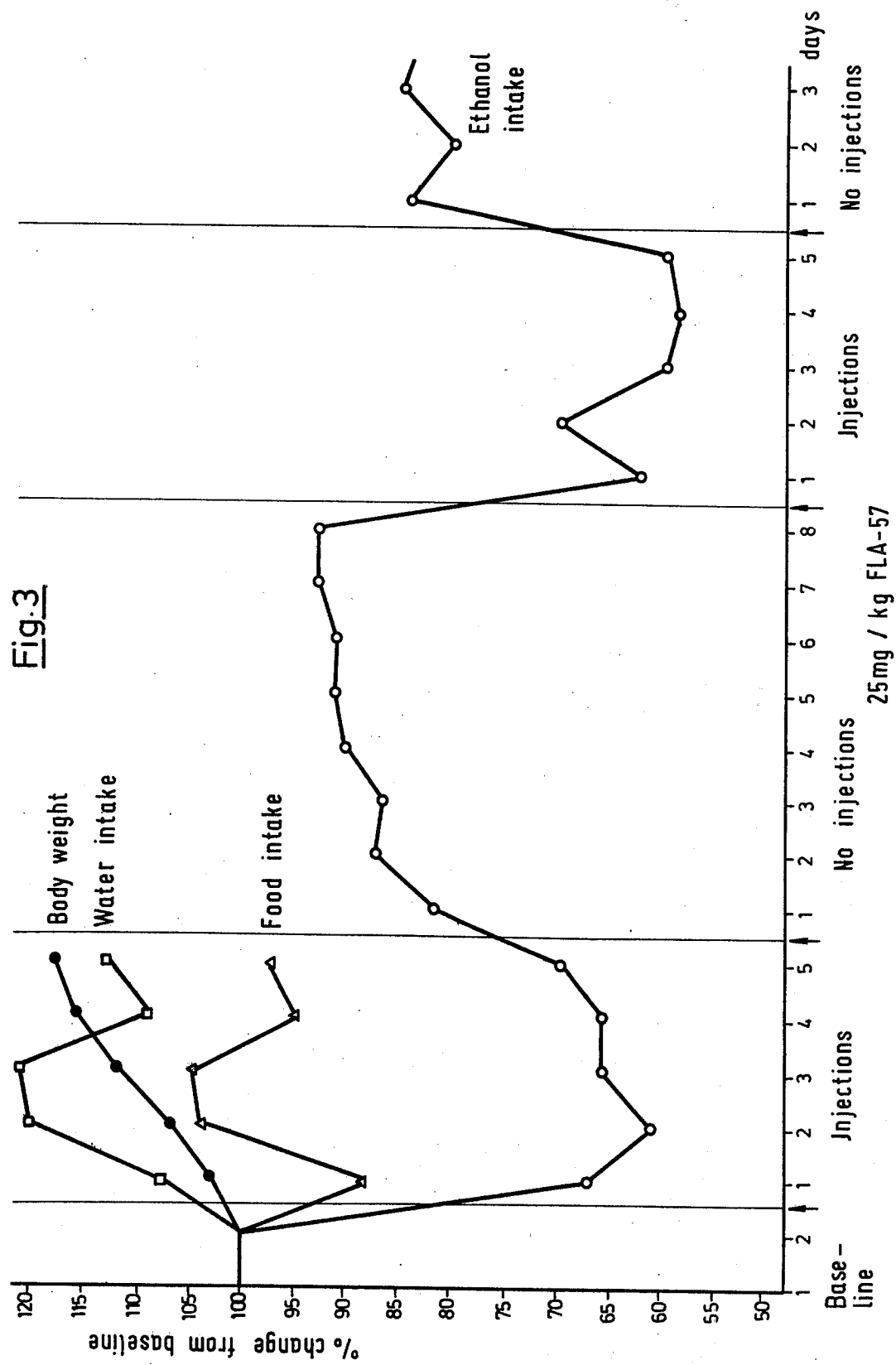
Figure 4:
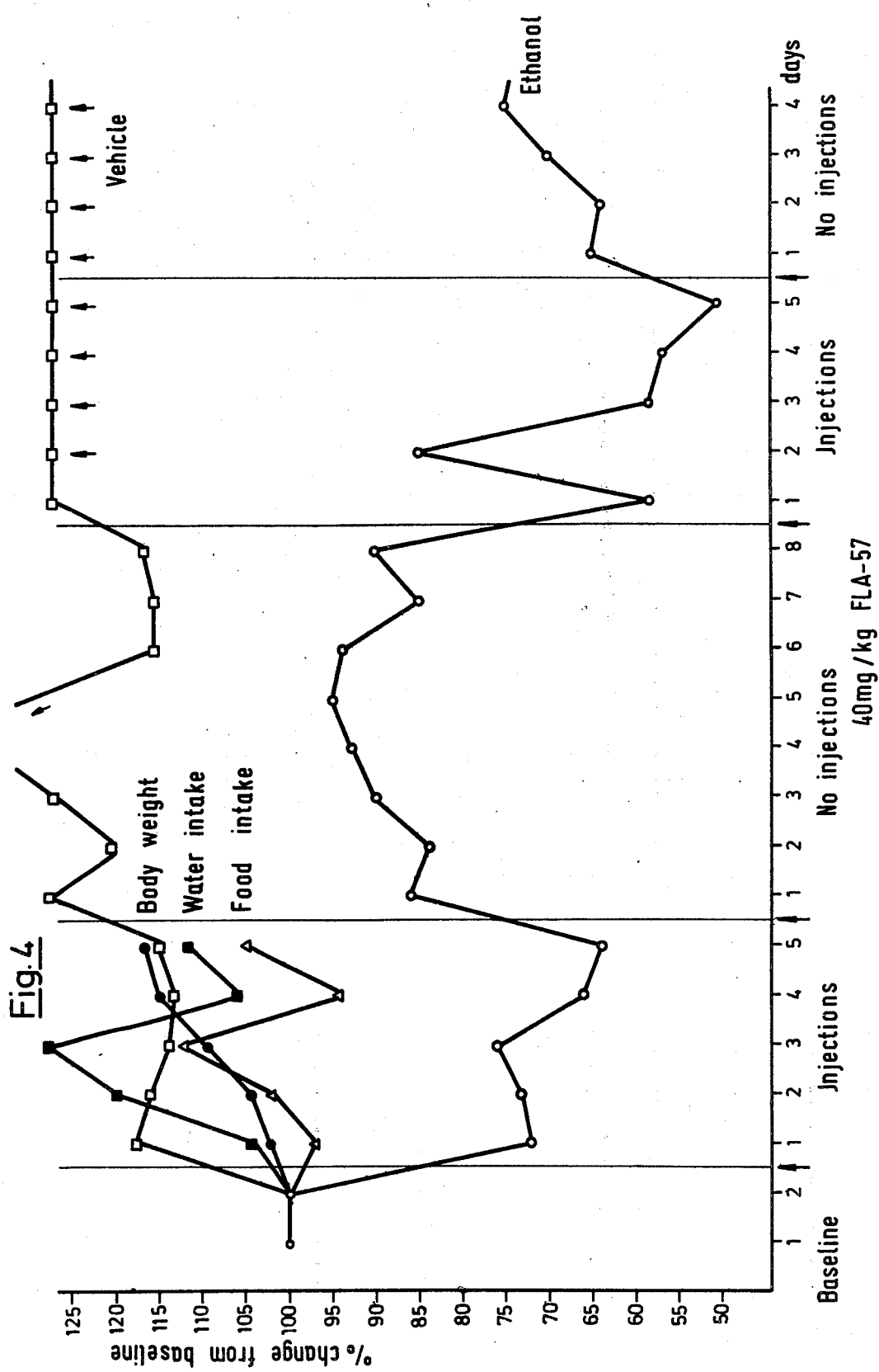
Figure 5:
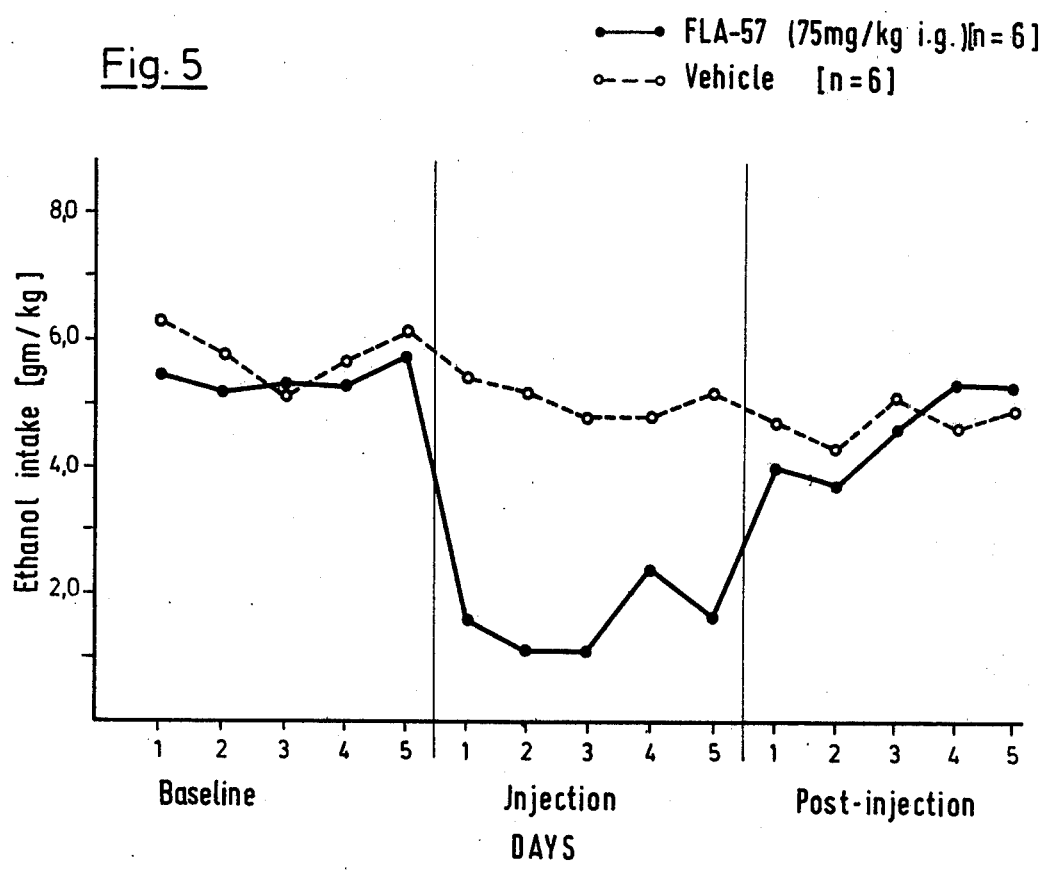

As can be seen from FIGS. 3 & 4, both doses of FLA-57 caused reduction in ethanol intake of approximately 35%-40% of baseline. Intake of ethanol during the first non-injection period quickly returned to near baseline. During the second injection period, intake of ethanol following 25 mg/kg of FLA-57 was once again reduced to 60% of baseline, while the 40 mg/kg dose reduced ethanol intake by 50%. In the final no-injection period, ethanol intake in the 25 mg/kg group recovered to approximately 80% of baseline, while the 40 mg/kg group recovered to approximately 70% of baseline. Vehicle injections had no effect on ethanol intake throughout the experiment. Furthermore, there were no decreases in water intake or body weight in any groups throughout the study.

A summary of the data obtained thus far can be interpreted to mean that FLA-57 in its action as a dopamine-beta-hydroxylase inhibitor at the dose levels employed in this study had a specific suppressant effect on ethanol intake in ethanol-preferring rats. This effect was independent of any possible effects on consummatory behaviours.

We further studied the effects of FLA-57 injection intragastrically on ethanol intake. In this experiment we examined the effects of FLA-57 injected directly into the stomach on ethanol consumption.

Procedure: Male Wistar rats were surgically implanted with a polyethylene tube into the stomach. Animals were then screened to drink ethanol (15% v/v) in a free-choice with water. Intragastric injection of FLA-57 (75 mg/kg — 15 mg/ml × 5) were administered for 5 consecutive days 3-4 hours prior to ethanol presentations.

Results: See FIG. 5 - ethanol intake (gm/kg).

Comments: Ethanol consumption was markedly attenuated by intragastrical administration of FLA-57.

Having demonstrated that FLA-57 injections are capable of attenuating ethanol consumption we attempted to produce extinction of ethanol drinking so that intake would remain suppressed after termination of FLA-57 injections.

Procedures:

Experiment A: Male Wistar rats were screened to drink a 15% v/v ethanol solution in a free-choice with water on alternate days. After establishing a stabilized baseline intake, animals were injected with either FLA-57 (30 mg/kg i.p. — 15 mg/ml × 2) or vehicle for 10 alternate days during which both drinking tubes were filled with ethanol. Injections were administered 3–4 hours prior to presentation of ethanol. Ethanol consumption in a free-choice with water was then recorded for 10 alternate days. The FLA-57 treatment was then administered as before but for only 5 instead of 10 alternate days.

Experiment B: Animals were treated in the same manner as in Experiment A except that the treatment phase consisted of 20 FLA-57 injections with ethanol available in a free-choice on days 1 and 17–20 and in a forced-choice on days 2–16. FLA-57 was injected in a dose of 60 mg/kg i.p. (15 mg/ml × 4) on the alternate days 3–4 hours prior to presentation of the drinking fluids.

Figure 6:
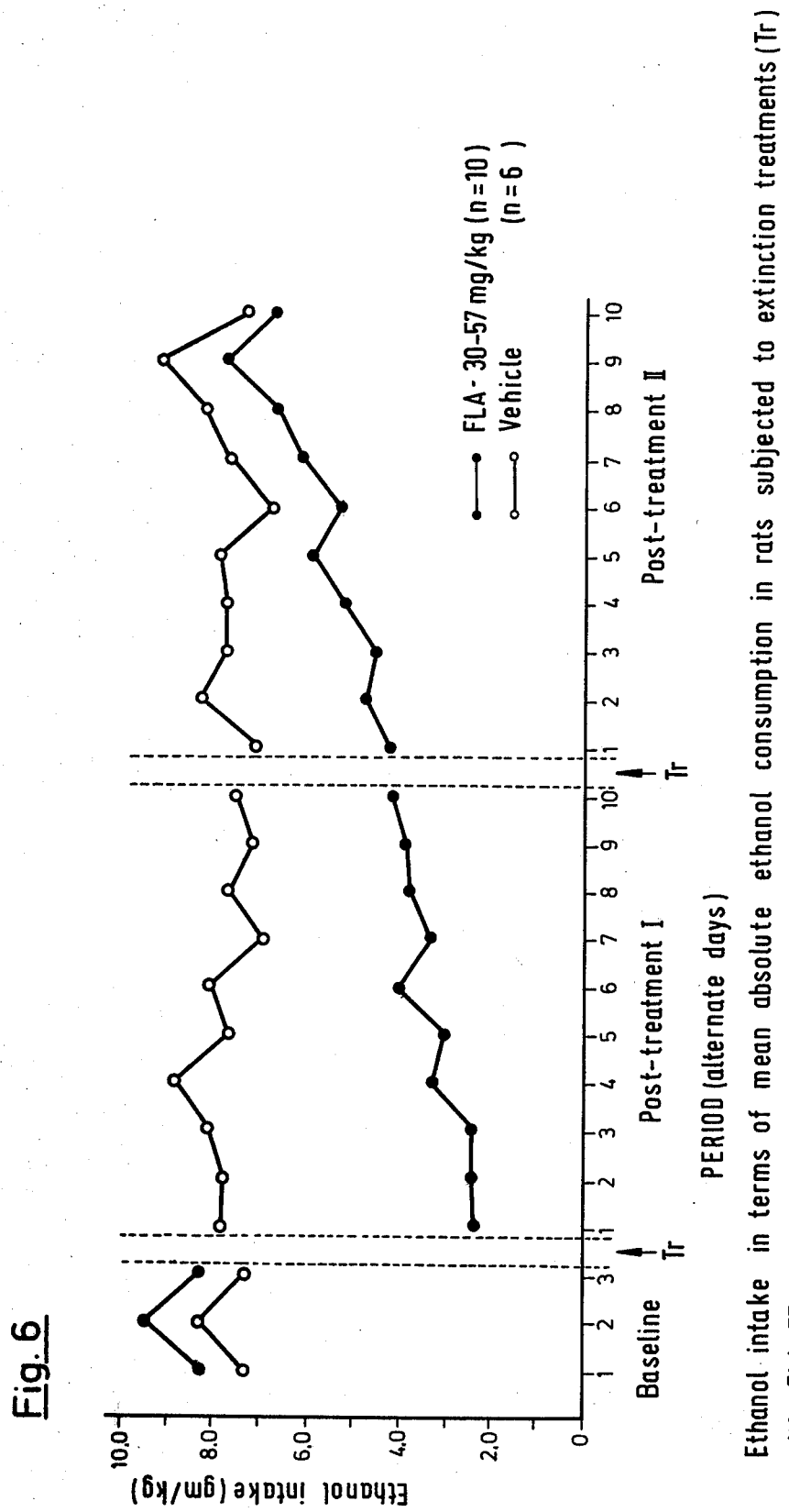
Figure 7:
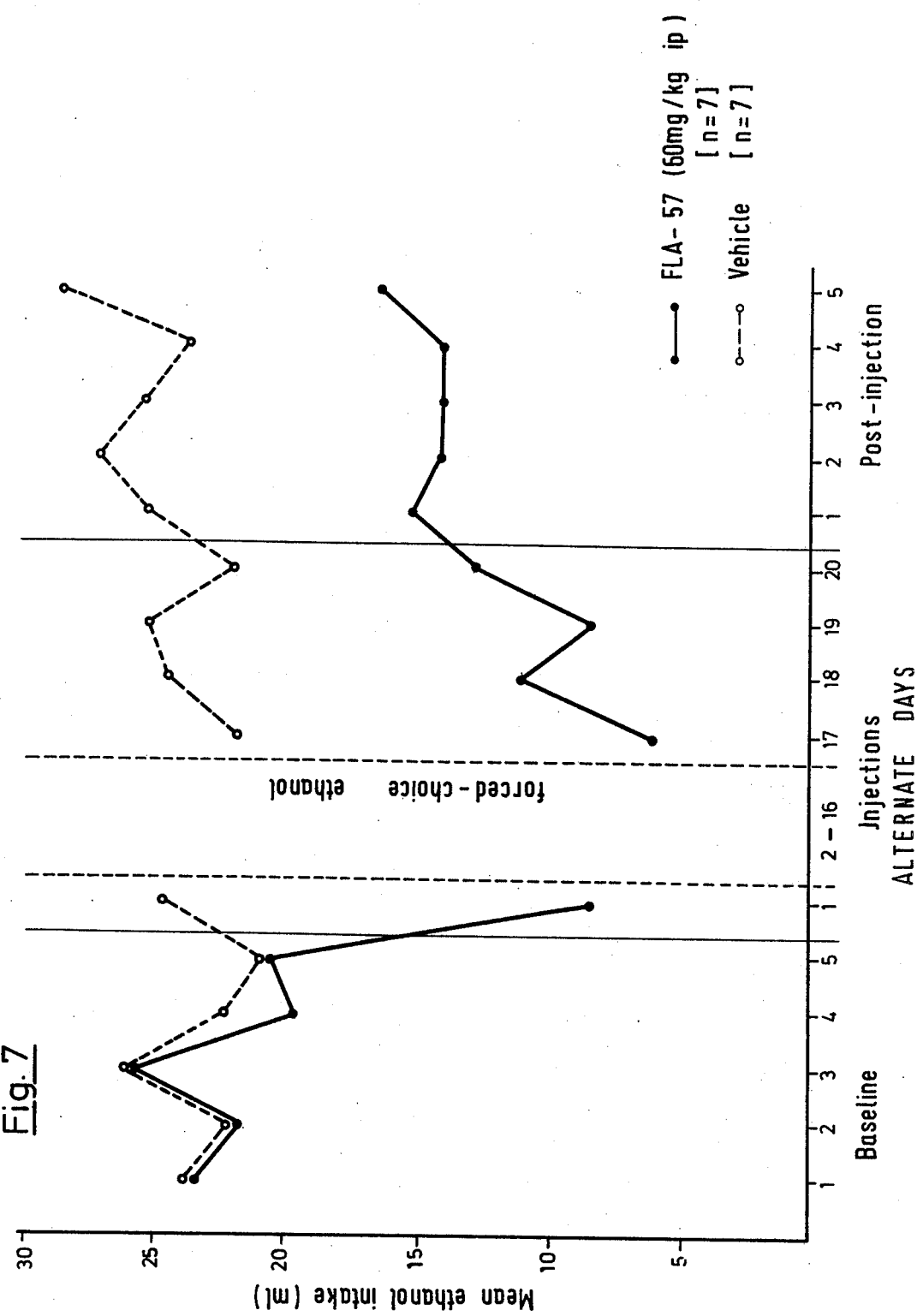

Results:

Experiment A: See FIG. 6 Ethanol Intake (g/kg)
Experiment B: See FIG. 7 Ethanol Intake (ml)

Comments: By forcing animals to drink ethanol while its reinforcing properties are suppressed by FLA-57 treatments, true extinction of ethanol drinking was produced. The suppression of ethanol drinking in Experiment B was not as strong as in Experiment A despite the more prolonged treatment period.

Finally the effects of FLA-57 injections (i.p.) on ethanol induced motor activity were studied.

In this experiment we tested the effects of FLA-57 on ethanol induced excitation.

Procedure: Male Wistar rats were injected with either FLA-57 (45 mg/kg i.p. — 15 mg/ml × 3) or vehicle 4 hours prior to the testing session. Half the animals in each of the two groups were injected i.p. with ethanol (4 ml/kg of a 20% solution v/v) or saline 5 minutes prior to testing. Animals were individually observed in an open field for a period of 15 minutes.

Figure 8:
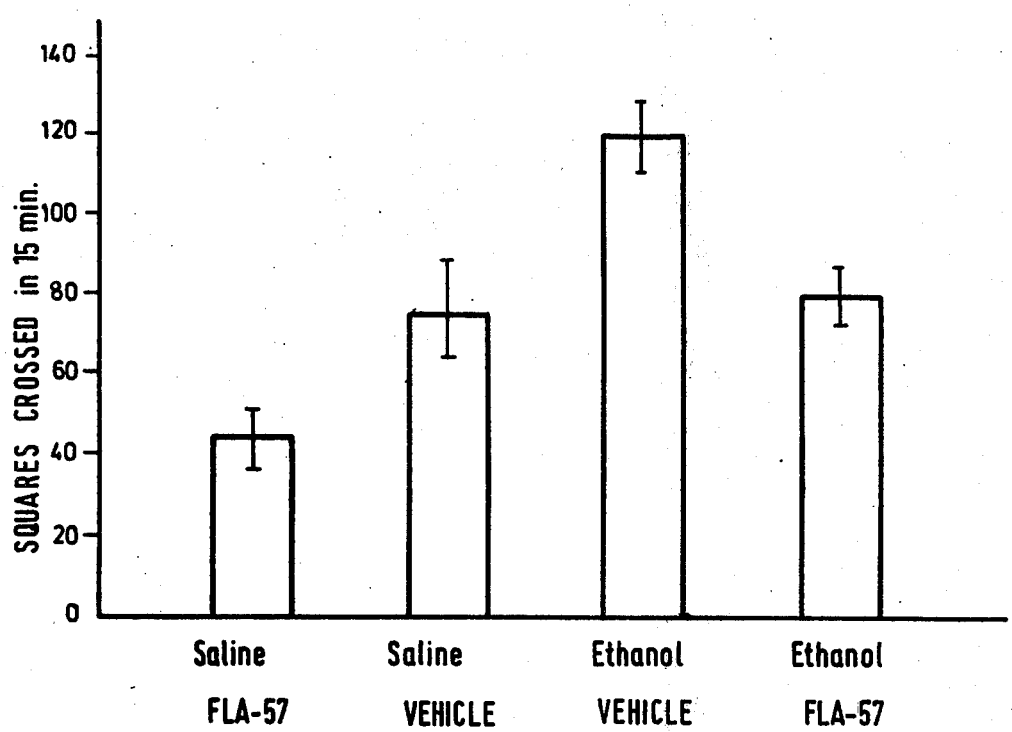

Results: See FIG. 8.

FLA-57 itself produced a slight but non-significant reduction in motor activity. The increased activity induced by ethanol was abolished by pretreatment with FLA-57.

In conclusion, the data reported in this application suggest that FLA-57 specifically suppresses ethanol intake via inhibition of dopamine-beta-hydroxylase. The mechanism by which dopamine-beta-hydroxylase inhibition exerts its influence on alcohol intake seems to be the blockade of the reinforcing properties of alcohol, most likely mediated by norepinephrine.

Further a preliminary study of the effects of FLA-57 on ethanol elimination and blood acetaldehyde levels was carried out. A comparison was made between FLA-63 and FLA-57 on these two measures. As stated previously, FLA-63 produced a significant elevation in blood acetaldehyde levels 30 minutes after injection. It also seemed to decrease the absorption of ethanol from the peritoneum. On the other hand, FLA-57 had no effect on either blood acetaldehyde levels or the rate of ethanol elimination.

TABLE I

FLA-57
Dose Response Curve
Animals received one injection and were killed 4 hrs. later.
Values are expressed in group means as percent of
Control. N = 4 in each group.

| NE | DA |
|---|---|
| Control = 100% | All DA values are normal |
| Vehicle = 96% | |
| 15 mg/kg = 69% | |
| 25 mg/kg = 75% | |
| 40 mg/kg = 71% | |
| 50 mg/kg = 67.8% | |

TABLE 2

FLA-57
Chronic injections
Animals received from 1–5 injections of FLA-57 and were killed
4 hrs. after their last injection. The dose was 30 mg/kg. All
vehicle animals received 5 injections. Numbers are percent of
control. N = 4 in each group.

| NE | DA |
|---|---|
| Vehicle = 93% | Vehicle = 85% |
| 1 injection = 68% | 1 injection = 100% |
| 2 injections = 68% | 2 injections = 96% |
| 3 injections = 61% | 3 injections = 94% |
| 4 injections = 74.7% | 4 injections = 87% |
| 5 injections = 76% | 5 injections = 100% |

Injections were every second day.

We claim:

1. A method of reducing a preference for alcohol, comprising administering to a host having an acquired preference for alcohol an amount effective to reduce said preference of the compound defined by the structural formula

wherein R is a pharmacologically acceptable, non-toxic cation.

2. A method of reducing a preference for alcohol, comprising administering to a host having an acquired preference for alcohol an amount effective to inhibit the enzyme dopamine-beta-hydroxylase in the organism of a compound as defined in claim 1.

3. A method according to claim 1 comprising administering a compound of the formula given in claim 1 wherein R is hydrogen.

4. A method according to claim 1 wherein R is selected from the group consisting of hydrogen, sodium, potassium, and ammonium.

5. A method according to claim 2 comprising administering a compound according to claim 2 wherein R is hydrogen.

6. A method according to claim 2 wherein R is selected from the group consisting of hydrogen, sodium, potassium, and ammonium.

* * * * *